United States Patent [19]

Karpowycz

[11] Patent Number: 4,480,191

[45] Date of Patent: Oct. 30, 1984

[54] AUTOMATIC GAIN CONTROL FOR AN INFRARED SOURCE OF AN AUTOMOTIVE EMISSIONS ANALYZER

[75] Inventor: Ihor B. Karpowycz, Chicago, Ill.

[73] Assignee: Sun Electric Corporation, Crystal Lake, Ill.

[21] Appl. No.: 424,083

[22] Filed: Sep. 27, 1982

[51] Int. Cl.³ .............................................. G01N 21/17
[52] U.S. Cl. ................................................... 250/343
[58] Field of Search ......................................... 250/343

[56] References Cited

U.S. PATENT DOCUMENTS 3,678,269  7/1972  Malek ................................. 250/341
4,016,423  4/1977  Meyer ................................. 250/343

FOREIGN PATENT DOCUMENTS 1000070  11/1976  Canada ............................... 250/343

Primary Examiner—Janice A. Howell
Assistant Examiner—Constantine Hannaher
Attorney, Agent, or Firm—Allegretti, Newitt, Witcoff & McAndrews, Ltd.

[57] ABSTRACT

An automatic gain control circuit for driving a low mass infrared source used in an automotive exhaust gas emissions analyzer. A reference spectrum of radiant energy is monitored, demodulated and converted to an error signal to maintain the source at a constant energy output.

13 Claims, 1 Drawing Figure

AUTOMATIC GAIN CONTROL FOR AN INFRARED SOURCE OF AN AUTOMOTIVE EMISSIONS ANALYZER

BACKGROUND

The invention relates to an emissions analyzer which analyzes the concentration of various gases in the exhaust stream of an internal combustion engine, and more specifically to an automatic gain control for the infrared source used in such an emissions analyzer.

Heretofore, infrared radiation sources have been constructed with a relatively large mass which results in a long warm-up time for the analyzer to stabilize, particularly from a cold start condition.

It is the primary object of the present invention to provide a radiant-energy infrared source which has a fast warm-up time beginning from a cold start. This is achieved by automatic gain control of the infrared source.

It is yet another object of the present invention to provide a constant infrared energy output from a radiant energy source, despite a cooling effect from an airdraft impinging the source element or the effect of changing ambient temperature or other environmental factors that would lead to a change in the infrared energy emitted by the source, and consequently the signal output of the infrared detectors used in the equipment.

SUMMARY

A preferred embodiment of the system uses one detector and a spectral filter combination for each gas which is to be measured plus one detector and a spectral filter combination for an automatic gain control (AGC) to drive the source. The AGC filter is selected to be responsive in a spectral region where no spectral absorption takes place for any gas of interest. All detectors are mounted on a common plate, having good thermal conductive properties so that all detectors are maintained at the same temperature.

The multi-detector assembly is temperature stabilized by means of a temperature controller. Temperature control is provided because a drastic change of the detector signal output takes place with respect to a small change in detector temperature.

It should be understood that within the scope of the preferred embodiment, this temperature stabilization can be accomplished either by heating or cooling the infrared detectors, since the techniques for automatic gain control of the infrared source are applicable to either detector configuration. The temperature element (heater or cooler) is mounted in physical contact with the detector mounting plate and in turn with the detectors.

The important benefit of this entire scheme is that it provides a constant infrared energy output from a low mass, thermally fast responding source which can operate in broad ambient temperature environment, as well as compensate for sample cell contamination and other environmental factors during normal operation in an automotive service facility.

DESCRIPTION OF THE PREFERRED EMBODIMENT

Figure 1:
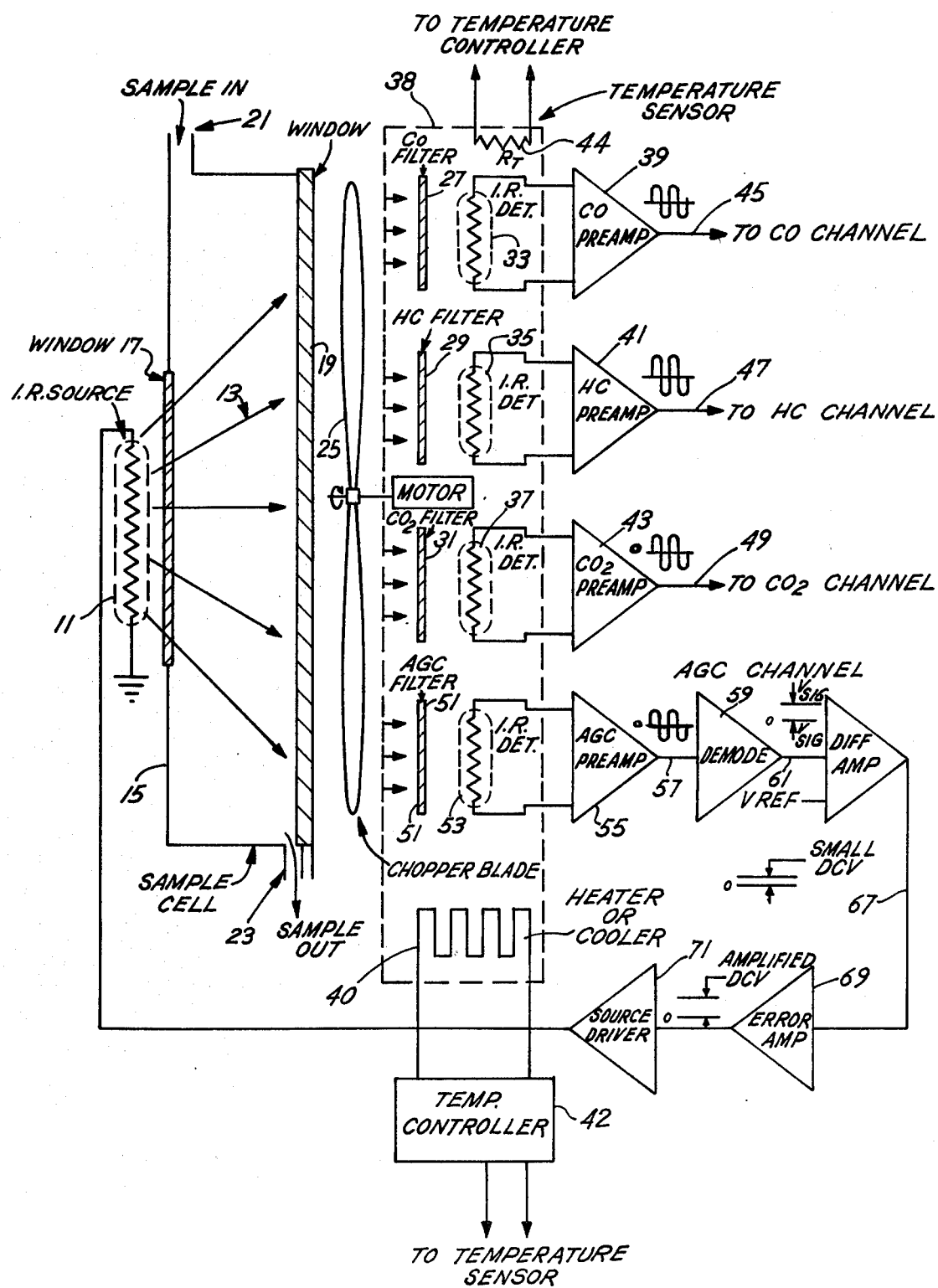
FIG. 1 is a partial block and schematic diagram of a preferred embodiment of the present invention.

Referring to FIG. 1, an infrared source 11 generates infrared radiant energy, as indicated by reference numeral 13, across a sample cell 15. A pair of windows 17, 19 are disposed on opposite sides of cell 15 for permitting the radiant energy to pass through the cell. A pair of openings 21, 23 are formed in the cell at opposite ends of the other sides, as shown, for providing a path of entry and exit of a sample gas through the cell.

The sample gas which passes through the cell is to be monitored for measuring the percentages of different component gases within the sample gas. The system is preferably used to analyze the exhaust gas of an internal combustion engine. Such a gas will contain carbon dioxide $CO_2$, carbon monoxide CO, Hydrocarbons HC, sulfur dioxide $SO_2$, oxides of nitrogen $NO_x$, and water vapor.

A chopper blade 25 is positioned outside the cell in close proximity to window 19 for chopping the radiant energy passing through the cell as the blade is rotated. A CO filter 27, an HC filter 29, a $CO_2$ filter 31 and an AGC filter 51 are positioned to the back side of chopper blade 25 for receiving and filtering the chopped energy radiation. Each filter 27, 29, 31 and 51 filters out all but a particular band of wavelengths of radiant energy associated with its respective gas. As understood, the wavelengths are associated with the gas absorption characteristics of the particular gas. Filter 51 is a neutral filter and its spectral response is on a wavelength where no gas absorption takes place. Its function is to monitor the infrared source energy output.

As infrared radiation passes through sample cell 15, the sample gas absorbs radiant energy at different wavelengths depending upon the particular type of component gases in the sample gas. No gas absorption occurs in the spectral region of filter 51. The particular absorption band related to a component gas is passed by its associated filter 27, 29, 31. The neutral band is free from any spectral absorption and is passed unchanged by its associated filter 51.

Four infrared detectors 33, 35, 37 and 53 are positioned relative to one of the filters 27-51 for detecting radiant energy passed by its associated filter. Each infrared detector 33-37 and 53 includes a resistive element across which a voltage potential is impressed. The resistive element changes in resistance in accordance with the radiant energy impinging the resistive element.

Thus, if the current through the resistive element is kept constant, the change in voltage across the resistive element is indicative of the quantity of radiant energy impinging the resistive element. Alternatively, when the voltage is kept constant, the current through the resistive element is indicative of the radiant energy received by the resistive element.

The four infrared detectors are placed in a detector assembly 38 and are temperature stabilized by a heating (or thermoelectric cooling) element 40 by means of a temperature controller 42. A temperature sensor 44 implanted in the heated (or cooled) detector assembly 38 monitors the temperature and feeds the information to the controller which applies power to the heating (or cooling) element 40 as required to maintain a constant detector operating temperature.

Three amplifier circuits 39, 41, 43 (the AGC circuit associated with filter 51 and detector 53 will be described in detail later) are connected across respective resistive elements 33, 35, 37 in order to develop thereacross a signal having a constant signal characteristic, e.g., current. Amplifier circuits 39, 41, 43 generate an output signal having a varying signal characteristic, e.g., voltage, along leads 45, 47, 49 which signal provides an indicating signal representative of the percentage of a particular gas within the sample gas passing through cell 15. The output signal is an A.C. signal due to chopper blade 25.

A particular circuitry configuration for an amplifier circuit 39, 41, 43 is illustrated in copending application Ser. No. 424,082, filed on September, 1982, in the name of the inventor of this application. However, any type of amplifier circuit may be utilized which generates an output signal having a signal characteristic which is representative of the quantity of radiant energy received by its associated detector. The simplest circuit would include a constant current source passing through the resistive element of the detector, with the output lead receiving the voltage across the detector.

The above described assembly of filters 27, 29, 31, detectors 33, 35, 37 and amplifier circuits 39, 41, 43, when used with a large mass I.R. source, is conventional. The preferred embodiment of the present invention is a gain control loop for generating a power signal for driving a relatively small mass infrared source 11.

Automatic gain control filter 51 is utilized in the automatic gain control loop for filtering radiant energy wavelengths which are not of the spectral absorption of the component gases found in the sample gas. An infrared detector 53 is positioned relative to automatic gain control filter 51 for receiving radiant energy passing through filter 51. An automatic gain control preamplifier 55, similar to amplifier circuits 39, 41, 43, develops a signal output indicative of the radiant energy received by infrared detector 53. As radiant energy is chopped by a chopper blade 25, automatic gain control preamplifier 55 develops an oscillating signal along an output conductor 57. The oscillating signal is graphically illustrated above conductor 57 on the drawing.

The signal appearing on conductor 57 is received by a demodulator 59 which converts the signal appearing on conductor 57 to a D.C. voltage signal level $V_{sig}$ along output conductor 61. Demodulator 59 may be constructed from a precision rectifier or a conventional rectifier to convert the A.C. signal to D.C. The D.C. level on conductor 61 is compared by a differential amplifier 63 with a reference voltage $V_{ref}$ at 65. Differential amplifier 63 serves to generate a difference signal (error signal) on an output conductor 67 which represents the difference in voltage level between the D.C. signal $V_{sig}$ on conductor 61 and the voltage signal $V_{ref}$ appearing on conductor 65.

The voltage signal developed along conductor 67 is fed to an error amplifier 69 which is a conventional amplifier for amplifying the error signal. The amplified error signal is then fed to a source driver 71 which produces an output voltage across I.R. source 11 to ground. Source driver 71 serves as a power drive for driving I.R. source 11. Source 11 includes a low mass heater element which provides a fast thermal response.

Automatic gain control filter 51 has a band pass between 3.8-3.9 micrometers (microns). As will suggest itself, automatic gain control filter 51 has a band pass which is absent from the spectral absorption of hydrocarbons, carbon monoxide, carbon dioxide, sulfur dioxide, oxides of nitrogen and water vapor, which are the components of the exhaust gas.

When the power is turned on, the source element of I.R. source 11 begins to warm up, resulting in an increase of infrared spectral emissions. Simultaneously the detector heater (or cooler) temperature stabilizes the detector assembly to a specifically predetermined temperature. The I.R. energy passes through the sample cell, and specific spectral bands, characteristic to separate gas components, are absorbed leaving the reference spectrum (3.8-3.9 microns) unchanged. The I.R. energy is chopped by chopper blade 19 and enters through the respective filters to each of the gas detectors. Each detector generates an output A.C. signal. The generated signal is amplified by each corresponding preamplifiers 39, 41, 43 and enters an analyzing channel for further processing. The automatic gain control signal from preamplifier 55, however, is demodulated to a D.C. signal level and continuously compared to the reference voltage $V_{ref}$.

Any positive or negative difference signal from the differential amplifier 63 is filtered and amplified by the error amplifier which in turn controls the source driver. As long as $V_{sig}$ is smaller than $V_{ref}$, the source output continues to increase until $V_{sig}$ is equal to $V_{ref}$. If, for some reason the source output is greater than required, the $V_{sig}$ will be greater than the $V_{ref}$, resulting in a positive error voltage which in turn will decrease the source drive. If, for other reasons, the source output is smaller than required, $V_{sig}$ will be smaller than $V_{ref}$ resulting in a negative error voltage which in turn will increase the source drive, and thus the source is maintained at a constant spectral output level.

It should be understood, of course, that the foregoing relates to a description of the preferred embodiment of the invention and that other modifications may be made therein as will suggest itself without departing from the spirit or scope of the invention as set forth in the accompanying claims.

What is claimed is:

1. An automatic gain control for driving a radiant energy source and controlling a constant energy emission for an automotive emission measurement system having a chopper means for chopping radiant energy passing from the source through a gas to be measured and onto a radiant energy detector, comprising:

a gain control filter for passing chopped radiant energy of preselected wavelengths;

radiant energy detector means positioned for receiving radiant energy passed by said control filter, said detector means generating a detector signal oscillating according to the chopping of the chopper means;

detector temperature controlling means for maintaining a temperature stable detector signal output of said radiant energy detector means, said detector temperature controlling means including detector temperature measuring means for monitoring the relative temperature of said radiant energy detector means;

demodulation means for demodulating said detector signal and generating a demodulated D.C. signal;

comparator means for comparing said demodulated D.C. signal with respect to a reference signal level for generating an error signal; and means responsive to the amplitude of said error signal for driving said infrared source.

2. An automatic gain control for driving a radiant energy source and controlling a constant energy emission for an automotive emission measurement system having a chopper means for chopping radiant energy passing from the source through a gas to be measured and onto a radiant energy detector, comprising:

a gain control filter for passing chopped radiant energy of preselected wavelengths;

radiant energy detector means positioned for receiving radiant energy passed by said control filter, said detector means generating a detector signal oscillating according to the chopping of the chopper means;

demodulation means for demodulating said detector signal and generating a demodulated D.C. signal;

comparator means for comparing said demodulated D.C. signal with respect to a reference signal level for generating an error signal; and means responsive to the amplitude of said error signal for driving said infrared source.

3. An automatic gain control according to claim 1 wherein said gain control filter filters out radiant energy of absorption bands of expected component gases in the gas to be measured whereby the radiant energy from the source is monitored for constant output maintenance.

4. An automatic gain control according to claim 1 wherein said radiation detector means includes photoresistive means for providing a change in resistance responsive to incident radiant energy, said photoresistive means serving as a means for generating a signal to be processed for automatically controlling the gain of the radiant energy source.

5. An automatic gain control according to claim 4 wherein said radiant energy detector means includes a preamplifier for developing a signal across said photoresistive means.

6. An automatic gain control according to claim 1 wherein said demodulation means includes rectifier means.

7. An automatic gain control according to claim 1 wherein said comparator means includes a differential amplifier.

8. An automatic gain control according to claim 1 wherein said means responsive to said error signal includes a driver means responsive to said error signal for generating a power signal across the radiant energy source.

9. An automatic gain control means according to claim 1 and further including a sample cell through which the gas is passed, said sample cell including a sample cell window through which radiant energy passes, said automatic gain control means compensating for loss in radiant energy passing through the cell due to sample cell window contamination resulting from normal operation in an automotive environment.

10. An automatic gain control according to claim 1 and further including a plurality of radiant energy detectors with associated gas absorption spectral filters, and wherein said detector temperature controlling means maintains temperature stable detector signal outputs of said plurality of radiant energy detectors.

11. An automatic gain control according to claim 10 wherein said detector temperature controlling means including a temperature element for changing the temperature of said radiant energy detector means.

12. An automatic gain control according to claim 11 wherein a temperature controller as means of controlling said detector temperature controlling means controls the detectors' temperature affected by ambient variations.

13. An automatic gain control according to claim 10 wherein said detector temperature measuring means includes a temperature sensor.

* * * * *